US007138582B2

(12) United States Patent
Lessar et al.

(10) Patent No.: US 7,138,582 B2
(45) Date of Patent: Nov. 21, 2006

(54) MEDICAL ELECTRICAL LEAD CONDUCTOR FORMED FROM MODIFIED MP35N ALLOY

(75) Inventors: Joseph F. Lessar, Coon Rapids, MN (US); Kenenth E. Cobian, St. Anthony, MN (US); Peter B. McIntyre, Mounds View, MN (US); David W. Mayer, Bloomington, MN (US)

(73) Assignee: Medtronic, Inc., Minneapolis, MN (US)

( * ) Notice: Subject to any disclaimer, the term of this patent is extended or adjusted under 35 U.S.C. 154(b) by 587 days.

(21) Appl. No.: 10/601,472

(22) Filed: Jun. 24, 2003

(65) Prior Publication Data

US 2004/0267107 A1    Dec. 30, 2004

(51) Int. Cl.
*H01B 5/00*    (2006.01)
(52) U.S. Cl. .................................. 174/126.1
(58) Field of Classification Search ............ 174/102 R, 174/102 A, 103, 106 R, 107, 108, 110 R, 174/113 R, 113 C, 117 R, 120 R, 126.1, 174/126.2
See application file for complete search history.

(56) References Cited

U.S. PATENT DOCUMENTS

| | | | | |
|---|---|---|---|---|
| 4,355,646 A * | 10/1982 | Kallok et al. | ............... | 607/122 |
| 4,591,393 A * | 5/1986 | Kane et al. | ................. | 148/707 |
| 5,246,014 A | 9/1993 | Williams et al. | ............ | 607/122 |
| 5,411,545 A | 5/1995 | Breyen et al. | ............... | 607/122 |
| 5,423,881 A | 6/1995 | Breyen et al. | ............... | 607/122 |
| 5,433,744 A * | 7/1995 | Breyen et al. | ............... | 607/125 |
| 5,483,022 A * | 1/1996 | Mar | ........................ | 174/128.1 |
| 5,760,341 A | 6/1998 | Laske et al. | ............. | 174/126.2 |
| 6,061,598 A * | 5/2000 | Verness et al. | ............. | 607/122 |
| 6,187,045 B1 | 2/2001 | Fehring et al. | ........... | 623/11.11 |
| 6,248,955 B1 * | 6/2001 | Avellanet | ................. | 174/128.1 |
| 6,539,607 B1 | 4/2003 | Fehring et al. | ................ | 29/557 |
| 6,720,497 B1 * | 4/2004 | Barsne | .................... | 174/102 R |
| 7,015,392 B1 * | 3/2006 | Dickenson | .................... | 174/36 |
| 2002/0068965 A1 * | 6/2002 | Sass | ............................ | 607/122 |
| 2002/0147488 A1 * | 10/2002 | Doan et al. | .................. | 607/122 |
| 2005/0004643 A1 * | 1/2005 | Ebert et al. | .................. | 607/122 |
| 2005/0027342 A1 * | 2/2005 | Shoberg et al. | ............. | 607/122 |

OTHER PUBLICATIONS

ASTM, Standard Specification for Wrought 35Cobalt-35Nickel-20Chromium-10Molybdenum Alloy for Surgical Implant Applications *UNS R30035), Jun. 2002, entire publication document.*
Cockcroft, S. et al., "Inclusions and the EB Refining of Superalloys," *Proceedings of the Conference, Electron Beam Melting and Refining State of the Art 1992, John K. Tien Memorial Conference,* p. 143-159 (1992).
Koenig, R., "The Federal Aviation Administration's (FAA's) Approach to Turbine Engine Certification as it Applies to Critical Titanium Components," *Proceedings of the Conference, Electron Beam Melting and Refining State of the Art 1991,* p. 27-30 (1991).

(Continued)

*Primary Examiner*—William H. Mayo, III
(74) *Attorney, Agent, or Firm*—Carol F. Barry; Girma Wolde-Michael

(57) ABSTRACT

A medical electrical lead having an elongated conductor including one or more wires made of a modified MP35N alloy. The modified MP35N alloy is formed from a melt composition modified to reduce an amount of titanium-based inclusion forming elements.

18 Claims, 5 Drawing Sheets

OTHER PUBLICATIONS

ASTM F 1058-02 Standard Specification for Wrought 40Cobalt-20Chromium-16Iron-15Nickel-7Molybdenum Alloy Wire and Strip for Surgical Implant Applications (UNS R30003 and UNS R30008), *ASTM International* (Apr. 10, 2002).

ASTM F 562-02 Standard Specification for Wrought 35Cobalt-35Nickel-20Chromium-10Molybdenum Alloy for Surgical Implant Applications (UNS R30035), *ASTM International* (Apr. 10, 2002).

* cited by examiner

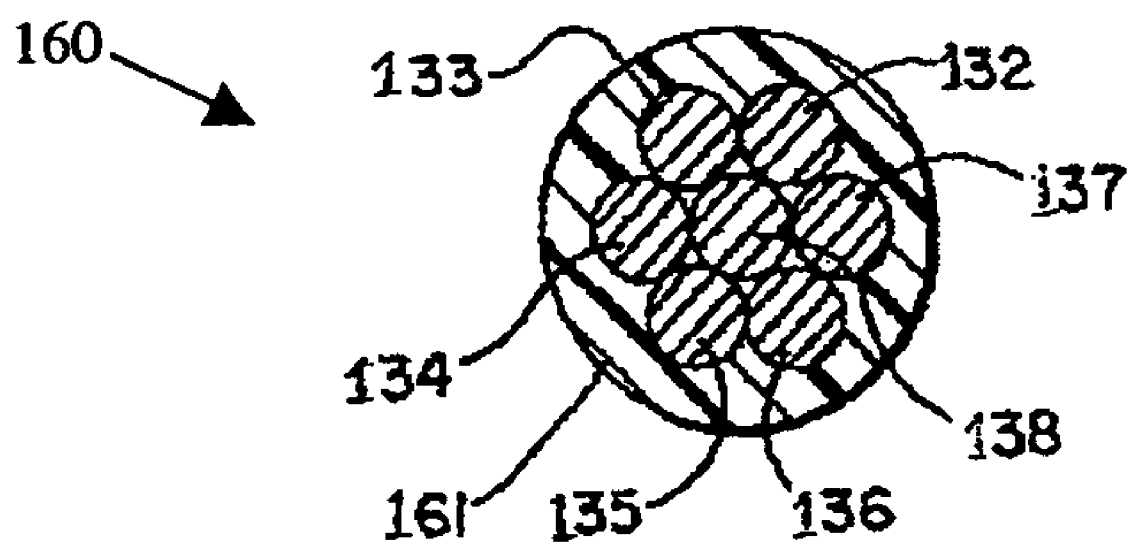

MEDICAL ELECTRICAL LEAD CONDUCTOR FORMED FROM MODIFIED MP35N ALLOY

FIELD OF THE INVENTION

The present invention relates to medical electrical leads and more specifically to conductors for such leads.

BACKGROUND OF THE INVENTION

Early cardiac pacemaker conductors were composed of numerous fine, stranded stainless steel wires. Marked improvement in both fracture rate and flexibility resulted when stainless steel conductors were wound into small coils with a hollow core. The hollow core of the coils also improved implantation since a stylet could be passed through the core during implantation to stiffen the lead. Corrosion resistance was significantly increased when stainless steel was replaced with more corrosion-resistant platinum iridium and nickel alloys such as Co—Ni—Cr—Mo alloy, available commercially as MP35N®, from Standard Pressed Steel Co., Jenkinstown, Pa. Highly specialized conductors were formed from such alloys such as multifilar coiled conductors and drawn, brazed strand wire. The use of multiple filars avoids the loss of electrical continuity in the event that one filar breaks. Drawn, brazed strand wire provides a low electrical resistance in a wire with high fatigue strength. Multifilar coils can also be used in side-by side or coaxial arrangements with insulation separating the conductors to provide individual conductors for the transmission of separate signals or stimulation pulses.

One limitation of commercially available alloys suitable for medical lead conductors, such as MP35N or Co—Cr—Ni—Fe—Mo—Mn alloy (known as Elgiloy®, from Elgiloy, Ltd.), is that foreign inclusions of nitride, oxide and/or carbide bodies present in the alloy negatively influence the metal fatigue life. Inclusions differ in mechanical and physical properties from the bulk alloy matrix. Titanium (Ti) is deliberately added to the MP35N alloy melt and is a significant carbide/nitride former. The inventors of the present invention have found titanium-nitride inclusions at or near fracture initiation sites of MP35N alloy wires that were rotary beam fatigue tested. Specifically, relatively hard, cubic titanium-carbide and titanium-nitride inclusions in excess of one micron in cross-section located within approximately three microns of the wire surface have been found to promote fatigue crack initiation in cold drawn wires having diameters between approximately 0.005 and approximately 0.010 inches in diameter.

The formation of oxide, carbide and nitride inclusions is related to melt practices employed in producing an alloy and casting it into ingot forms. Elgiloy develops oxide-based inclusions during vacuum induction melting and secondary melting during electro-slag refining, which occur under ambient atmospheric conditions allowing light metal oxides to reach equilibrium conditions. Sub- to multi-micron diameter oxide inclusions result. Formation of titanium-based inclusions in MP35N is a process not fully understood but is expected to be related to pressure, temperature, elemental concentrations, and other equilibrium-driving factors present during alloy melt practices.

As patient indications for cardiac pacing expands, new pacing systems are being developed, such as multi-chamber or biventricular pacing systems, that require the use of relatively small diameter leads. These systems can use multiple leads, and multiple electrodes may be carried on a single lead requiring multiple conductors. In order to implant multiple leads through a venous access point, or advance a single lead through a narrow, tortuous pathway such as the cardiac veins, very small diameter leads are desired. Leads are presently being manufactured having a diameter on the order of 2 to 4 French. In order to manufacture such small diameter leads, conductor wires must be drawn very fine, on the order of 0.001 inch or less. As conductor diameter is reduced, the impact of inclusions on fracture resistance becomes greater. It is desirable, therefore, to provide a corrosive-resistant conductor having low electrical resistance that has improved fatigue resistance due minimization of the number and/or size of foreign inclusions.

BRIEF DESCRIPTION OF THE DRAWINGS

FIGS. 3A–B are a cross-sectional views of exemplary cabled conductors for use in a medical electrical lead according to alternate embodiments of the present invention.

DETAILED DESCRIPTION OF THE EMBODIMENTS

Figure 1:
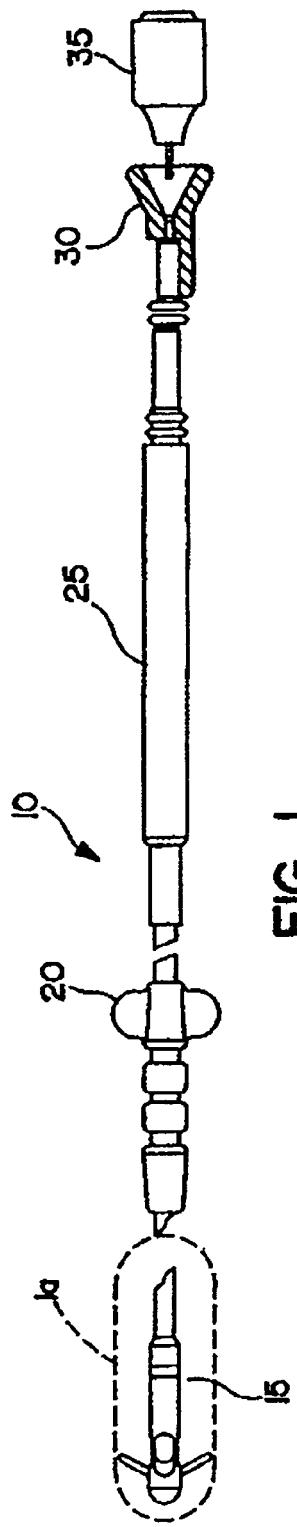
FIG. 1 is a plan view of a medical electrical lead system suitable for endocardial stimulation by an implantable heart pacemaker.

Processing methods for eliminating or minimizing titanium-based inclusions allow the material to retain excellent corrosion-resistance and other mechanical properties that make it a desirable choice for medical lead conductors. In the context of this disclosure, the terms 'low titanium-based inclusion Co—Ni—Cr—Mo alloy' and 'modified MP35N alloy' are used interchangeably to describe a Co—Ni—Cr—Mo super alloy having a relatively low or no titanium-based inclusion content according to embodiments of the present invention.

In one embodiment, a low titanium-based inclusion Co—Ni—Cr—Mo alloy is produced by eliminating titanium from the melt composition such that titanium is not available to form nitride, carbide or oxide inclusions during melt processes. Commercially available Co—Ni—Cr—Mo alloy, known as MP35N®, includes titanium in the alloy melt as a deliberate addition. The titanium addition may promote physical properties desirable for relatively large component fabrication but results in titanium-based inclusions that are undesirable in fine wire fabrication. During alloy melting at moderate vacuum levels in commercially available furnaces, for example during vacuum induction melting, electro-slag re-melting and vacuum arc refining, titanium-based inclusions form. By eliminating titanium from the melt composition, trace titanium content in the principle alloying metals and other unavoidable element contributions will result in acceptable inclusions of minimal size and number. Inclusion counts, on average, for the commercially available Co—Ni—Cr—Mo alloy, known as MP35N®, are 528,212 inclusions per square inch and for the low titanium-based inclusion Co—Ni—Cr—Mo alloy are 33,411 inclusions per square inch.

To form a low titanium-based inclusion Co—Ni—Cr—Mo alloy, each of the four principal elements are refined to form an ultra pure furnace charge stock. The refined principal elements are combined in an alloy melt by vacuum induction melting. Homogenization and final refining is performed in a vacuum arc refining laboratory. The alloy material produced in this way typically contains less than 0.001% titanium by weight in comparison to commercially available MP35N, which contains up to 1.0% titanium by weight. After standard cold processing methods, an intermediate drawn wire product specified to be 0.100 inches in diameter is produced. A fine wire product may then be formed through wire draw processing.

In an alternative embodiment of the present invention, altering melt practices to limit the formation of inclusions that would occur in a standard MP35N melt composition, which includes titanium, produces a low titanium-based inclusion Co—Ni—Cr—Mo alloy. Specifically, gaseous oxygen and nitrogen are eliminated by high vacuum operating conditions in an electron beam furnace during alloy melt fabrication. When processed in an electron beam furnace, or alternative by plasma melt refining, titanium-based inclusions, in particular titanium nitride, titanium carbide, and titanium oxides can be reduced in number and in size, at or below 1 micron in diameter. Reducing the size and number of nitride, carbide and oxide inclusions in the conventional alloy composition produces a material having greater fatigue-resistance.

Fatigue resistance testing has been performed on exemplary wires to evaluate low titanium-based inclusion Co—Ni—Cr—Mo alloy compared to commercially available MP35N for use as fine wire medical lead conductors. Stress versus number of cycles to rupture was determined during rotary beam, U-bend, wire spin tests of 0.007 inch diameter wire formed from low titanium-based inclusion Co—Ni—Cr—Mo alloy and two commercially available MP35N alloys. The results are listed in Table I below. The number of cycles to rupture was significantly greater for the wire samples formed from modified MP35N alloy produced from a titanium-free alloy melt compared to wire samples manufactured from commercially available MP35N alloy compositions obtained from two different sources.

TABLE I

| ALLOY | MEDIAN TENSILE STRENGTH, In 1000 psi | MEDIAN CYCLES TO RUPTURE, AT 90,000 psi |
| --- | --- | --- |
| Low Ti-inclusion (CarTech VIM-VAR) Co—Ni—Cr—Mo (p < 0.05) | 254 | 19 million |
| MP35N a (CarTech VIM-ESR-VAR) | 271 | 7 million |
| MP35N b (Latrobe VIM-VAR) | 269 | 2 million |

Figure 1A:
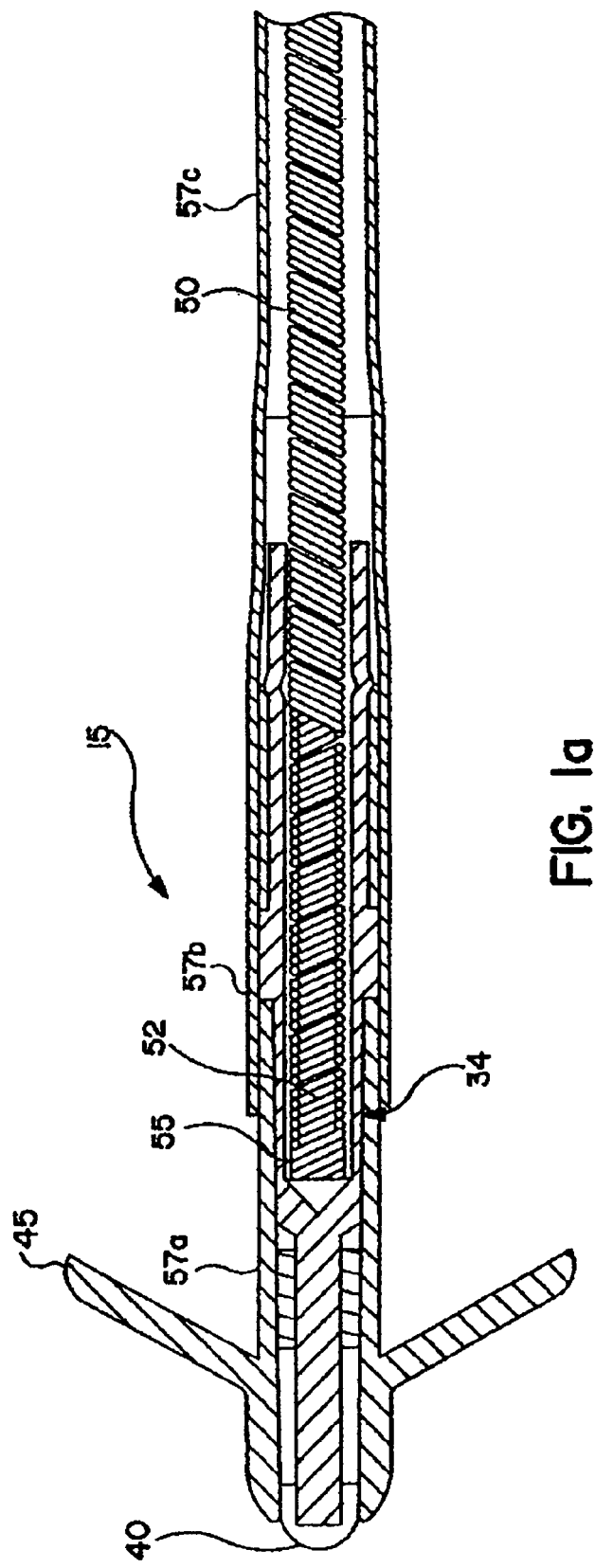
FIG. 1a is a cross-sectional view of a portion of the lead system of FIG. 1.
Figure 2A:
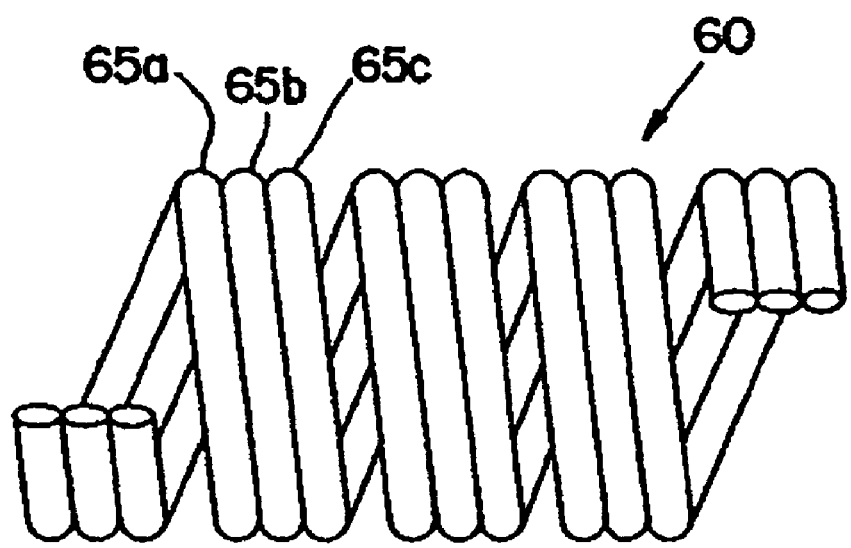
FIG. 2a is a plan view of a portion of a three-filar conductor winding for use in a medical electrical lead according to an embodiment of the present invention.
Figure 2B:
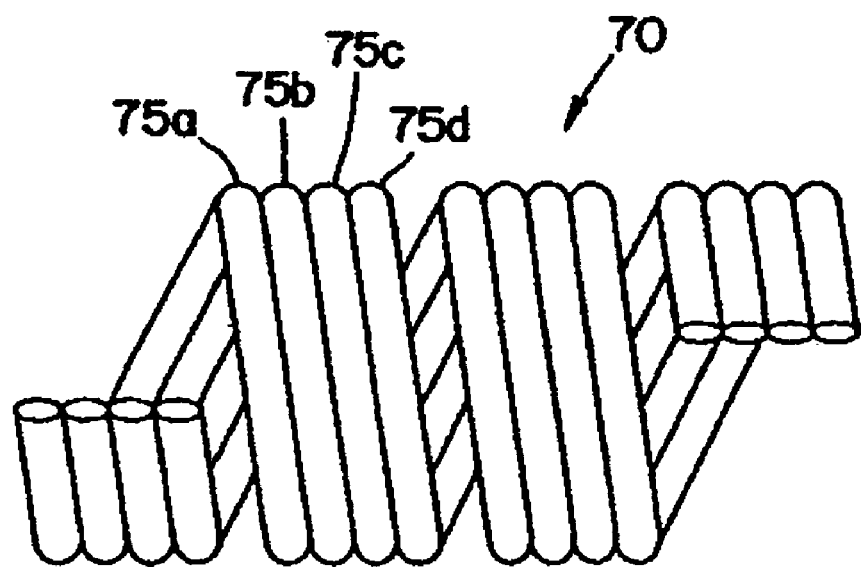
FIG. 2b is a plan view of a portion of a four-filar conductor winding for use in a medical electrical lead according to another embodiment of the present invention.

FIG. 1 is a plan view of a medical electrical lead system suitable for endocardial stimulation by an implantable heart pacemaker. FIG. 1 shows a lead system 10, which includes a lead assembly 15, an anchoring sleeve 20, a connector 25, a stylet guide 30, and a stiffening stylet 35. In FIG. 1a, the lead assembly is shown in greater detail with an electrode structure 40 at a distal end of the lead assembly 15, a tine 45 to secure the lead assembly 15 endocardially, a lead conductor 50 in a multifilar coil configuration which allows the stiffening stylet 35 to be inserted into the lead assembly 15 in the internal lumen 52 of the lead conductor 50. Lead conductor 50 is shown attached at its distal end 55 to the electrode structure 40 and is also similarly attached at a proximal end (not shown) to the connector 25. Alternate multifilar coil configurations are shown in FIGS. 2a and 2b as a three-filar coil 60 having individual wires 65a, 65b, and 65c and as a four-filar coil 70 having individual wires 75a, 75b, 75c and 75d. Insulation elements 57a, 57b, and 57c insulate portions of the electrode structure 40 and lead conductor 50. Such insulation elements 57a, 57b, and 57c may be made from conventional silicone, polyurethane or other biocompatible lead insulation materials. While a unipolar lead is shown and described above, the present invention can also be applied to bipolar or multipolar leads. As used in implantable pacing leads, the individual wires of the lead conductor would typically be about 0.004 to 0.010 inches in diameter, but could be as small as 0.0005 inch in diameter wound into extremely small coils, approximately 0.006 inch in diameter.

Conductors, such as conductors 50, 60, 70, in accordance with the present invention, are formed of modified MP35N alloy having a relatively low or no titanium-based inclusion content. Coiling modified MP35N alloy wire to make medical leads may be performed using the same methods used for coiling conventional MP35N alloy wire. Incorporation of such wires into a final lead assembly could involve welding to the connector and electrode materials since the materials presently used for those components are materials to which the modified MP35N alloy is generally weldable. Alternatively, crimping, staking, or other methods for joining the conductor to desired lead components may be used to form an electrical connection. In multi-conductor coils, the wires may be provided individually with a polymeric insulation material such as silicone, polyurethane, PTFE, ETFE, polyethylene, polypropylene, or other polymer coatings or tubing known for use in cardiac leads.

In alternative embodiments, conductors take the form of a single or bi-filar coiled conductor, or a stranded, cabled or straight wire conductor. Types of conductors, which may be formed using low titanium-based inclusion Co—Ni—Cr—Mo alloy, are generally disclosed in U.S. Pat. No. 4,355,646 issued to Kallok, which describes conductors arranged concentrically with intervening layers of insulation; U.S. Pat. No. 5,246,014, issued to Williams et al., which describes a cabled conductor; and U.S. Pat. No. 5,760,341 issued to Laske et al., which describes a cabled conductor, all of which patents are incorporated herein by reference in their entirety.

Figure 3B:
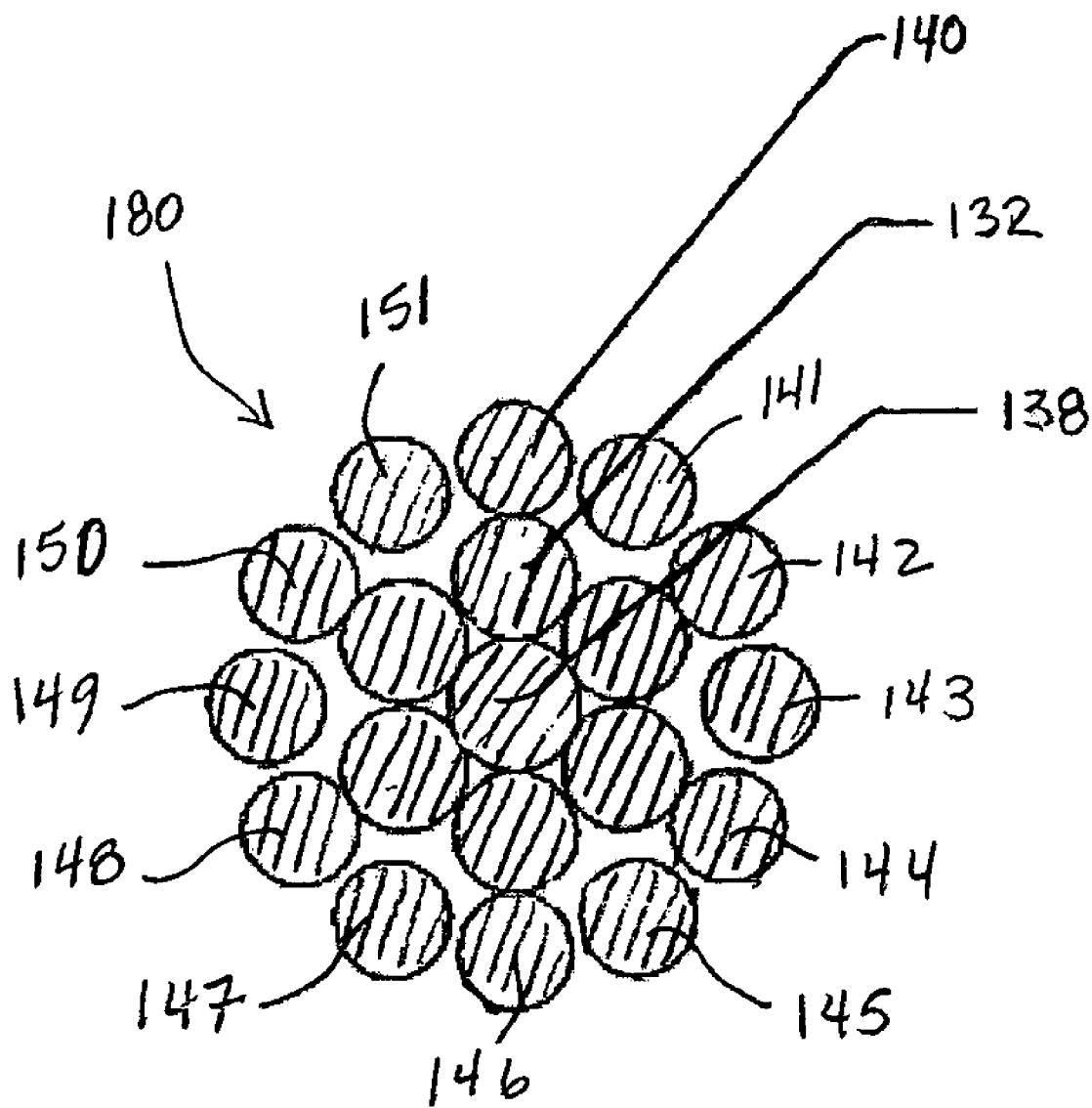

FIGS. 3A–B are a cross-sectional views of exemplary cabled conductors 160 and 180, respectively, for use in a medical electrical lead. Cabled conductor 160 includes strands 132 through 138 and cabled conductor 180 includes strands 132 through 151, any or all of which are formed from the low titanium-based inclusion Co—Ni—Cr—Mo alloy described above according to alternate embodiments of the present invention; a diameter of each strand in various embodiments is between approximately 0.0005 inch and 0.005 inch. In the embodiment shown in FIG. 3A, cabled conductor 160 is generally formed from a number of peripheral strands 132–137, which are arranged around a central, core strand 138. In the embodiment shown in FIG. 3B an additional layer of peripheral strands 140–151 are arranged around peripheral strands 132–137. Using a conventional stranding machine, strands 132–138 and strands 132–151 are each tightly bundled in a cable-like fashion to form unitary conductors 160 and 180, respectively. The lay or pitch of the stranding is typically between 0.3 inch and 0.6 inch. As illustrated in FIG. 3A, cabled conductor 160 may be enclosed in an insulating coating 161.

Figure 4:
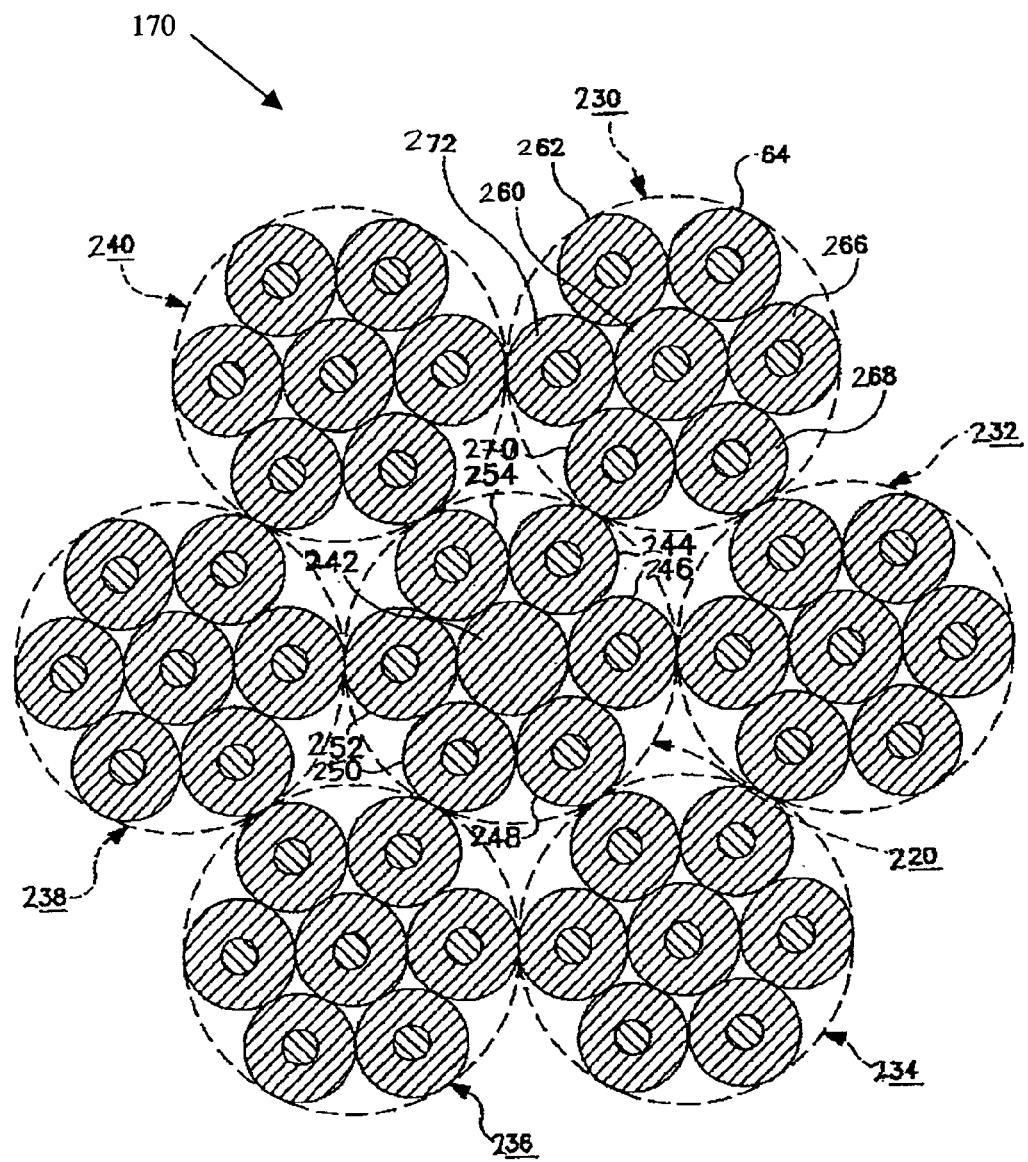
FIG. 4 is a cross-sectional view of an 7×7 conductor cable for use in a medical electrical lead according to another embodiment of the present invention.

FIG. 4 is a cross-sectional view of another exemplary cabled conductor 170 for use in a medical electrical lead and formed from a low titanium-based inclusion Co—Ni—Cr—Mo alloy according to an embodiment of the present invention. As illustrated in FIG. 4, cabled conductor 170 includes a core wire strand 220 formed of seven wires and surrounded by a number of perimeter wire strands 230, 232, 234, 236, 238 and 240 helically wound about the core wire strand 20 without overlapping one another and at a relatively constant and shallow pitch to form a relatively constant outer diameter of cabled conductor 170, which, according to various embodiments, is between approximately 0.005 inch and approximately 0.020 inch. The cabled conductor of FIG. 4 follows an M×N conductor cable configuration. The core wire strand 220 is formed of M=N, where N=7 in the depicted embodiment, wires including first core wire 242 and N–1 first peripheral wires 244, 246, 248, 250, 252 and 254 helically wound about first core wire 42 without overlapping one another and at a relatively constant wire pitch in a relatively constant diameter. The core wire strand 220 can be referred to as a 1×N cable, i.e., a 1×7 cable in the embodiment depicted. Each of the N–1 perimeter wire strands is similarly formed of N, in this example 7, wires including a second core wire and N–1, or 6, second peripheral wires helically wound about the second core wire in a manner as described above. Only the second core wire 260 and the second peripheral wires 262, 264, 266, 268, 270, and 272 of perimeter wire strand 230 are shown in detail, and it will be understood that the other five perimeter wire strands are formed in the same manner.

In an M×N conductor cable such as the conductor cable depicted in FIG. 4, the core wire strand 220 is relatively straight and subjected to a greater stress and strain on bending than the helically wrapped perimeter Wire strands 230, 232, 234, 236, 238, and 240. Therefore, core wire strand 220 is preferably formed from low titanium-based inclusion Co—Ni—Cr—Mo alloy for improved fatigue resistance. Any of first core wire 242 and first peripheral wires 244, 246, 248, 250, 252, and 254 used in forming core wire strand 220 may be fabricated from low titanium-based inclusion Co—Ni—Cr—Mo alloy. In addition, the helically wrapped, perimeter wire strands 230, 232, 234, 236, 238 and 240 may include second core wires and/or second peripheral wires formed from low titanium-based inclusion Co—Ni—Cr—Mo alloy. Furthermore, it is recognized that wires used in forming an M×N conductor cable may be formed of low titanium-based inclusion Co—Ni—Cr—Mo alloy cladding over a silver or gold core. A method of assembling an M×N conductor cable and other considerations, such as the relative diameters of wires included, is generally described in the above-cite U.S. Pat. No. 5,760,341, issued to Laske et al.

While particular embodiments are shown and described above, it is understood that a low titanium-based inclusion Co—Ni—Cr—Mo alloy conductor could be used to form other configurations of medical electrical lead conductors. It is further recognized that a conductor may be formed as low titanium-based inclusion Co—Ni—Cr—Mo alloy clad, silver core wire. Numerous types of medical electrical leads may benefit from the use of aspects of the present invention. Thus, it will be appreciated by those skilled in the art that numerous variations, uses and modifications of the described embodiments may be made. Hence, descriptions of particular embodiments provided herein are intended as exemplary, not limiting, with regard to the following claims.

What is claimed is:

1. A medical electrical lead comprising an elongated conductor including one or more wires made of a modified MP35N alloy;
   wherein the alloy being formed from a melt composition modified to reduce an amount of titanium-based inclusion forming elements;
   wherein the inclusion forming elements include titanium and the modification of the melt composition includes eliminating the titanium as an additive to the melt composition; and
   wherein the alloy comprises less than approximately 0.001% titanium by weight.

2. The medical electrical lead of claim 1, wherein the conductor being a coiled conductor.

3. The medical electrical lead of claim 1, wherein the conductor being a cabled conductor.

4. The medical electrical lead of claim 1, wherein a minimum diameter of the one or more wires being between approximately 0.0005 inch and approximately 0.01 inch.

5. The medical electrical lead of claim 4, wherein a minimum diameter of the one or more wires being between approximately 0.0005 inch and approximately 0.003 inch.

6. A medical electrical lead comprising an elongated conductor including one or more wires made of a modified MP35N alloy;
   wherein the alloy being formed from a melt composition modified to reduce an amount of titanium-based inclusion forming elements; and
   wherein the inclusion forming elements include a gaseous oxygen and nitrogen and the modification of the melt composition includes eliminating the gaseous oxygen and nitrogen under high vacuum conditions.

7. A medical electrical lead comprising an elongated conductor including one or more wires made of a modified MP35N alloy;
   wherein the alloy comprises less than approximately 0.001% titanium by weight.

8. The medical electrical lead of claim 7, wherein the conductor being a coiled conductor.

9. The medical electrical lead of claim 7, wherein the conductor being a cabled conductor.

10. The medical electrical lead of claim 7, wherein a minimum diameter of the one or more wires being between approximately 0.0005 inch and approximately 0.01 inch.

11. The medical electrical lead of claim 10, wherein a minimum diameter of the one or more wires being between approximately 0.0005 inch and approximately 0.003 inch.

12. A medical electrical lead comprising a conductor including one or more wires made of an MP35N alloy;
    wherein the one or more wires comprise titanium-based inclusions, an average number of which being less than 100,000 per square inch.

13. The medical electrical lead of claim 12, wherein the average number of titanium-based inclusions have a maximum diameter not exceeding approximately one micron.

14. The medical electrical lead of claim 12, wherein the conductor being a coiled conductor.

15. The medical electrical lead of claim 12, wherein the conductor being a cabled conductor.

16. The medical electrical lead of claim 12, wherein a minimum diameter of the one or more wires being between approximately 0.0005 inch and approximately 0.01 inch.

17. The medical electrical lead of claim 16, wherein a minimum diameter of the one or more wires being between approximately 0.0005 inch and approximately 0.003 inch.

18. A medical electrical lead comprising an elongated conductor including one or more wires made of a modified MP35N alloy; the alloy being formed from a melt composition modified to reduce an amount of titanium-based inclusion forming elements;
 wherein the inclusion forming elements include titanium, gaseous oxygen and nitrogen and the modification of the melt composition comprises eliminating the titanium as an additive to the melt composition and further comprises eliminating the gaseous oxygen and nitrogen under high vacuum conditions;
 wherein the alloy comprises less than approximately 0.001% titanium by weight, and
 wherein the one or more wires comprise titanium-based inclusions, an average number of which being less than 100,000 per square inch, having a maximum diameter not exceeding approximately one micron.

* * * * *